US008431585B2

(12) United States Patent
Singer et al.

(10) Patent No.: US 8,431,585 B2
(45) Date of Patent: Apr. 30, 2013

(54) USE OF INHIBITORS OF THE EGFR-MEDIATED SIGNAL TRANSDUCTION FOR THE TREATMENT OF BENIGN PROSTATIC HYPERPLASIA (BPH)/PROSTATIC HYPERTROPHY

(75) Inventors: Thomas Singer, Inzlingen (DE); Stefan Platz, Linkenheim-Hochstetten (DE); Florian Colbatzky, Stafflagen (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 73 days.

(21) Appl. No.: 12/706,819

(22) Filed: Feb. 17, 2010

(65) Prior Publication Data
US 2010/0144639 A1 Jun. 10, 2010

Related U.S. Application Data

(63) Continuation of application No. 11/609,407, filed on Dec. 12, 2006, now abandoned, which is a continuation of application No. 10/431,699, filed on May 8, 2003, now abandoned.

(60) Provisional application No. 60/389,815, filed on Jun. 18, 2002.

(30) Foreign Application Priority Data

May 11, 2002 (DE) ................... 102 21 018

(51) Int. Cl.
 *A61K 31/517* (2006.01)
(52) U.S. Cl.
 USPC ..................... 514/266.3; 514/266.4
(58) Field of Classification Search ............... 514/266.3, 514/266.4
 See application file for complete search history.

(56) References Cited

U.S. PATENT DOCUMENTS

| | | | |
|---|---|---|---|
| 5,866,572 A | 2/1999 | Barker et al. | |
| 6,127,374 A | 10/2000 | Bridges | |
| 6,153,617 A | 11/2000 | Bridges | |
| 6,251,912 B1 | 6/2001 | Wissner et al. | |
| 6,344,459 B1 | 2/2002 | Bridges et al. | |
| 6,362,336 B1 | 3/2002 | Lohmann et al. | |
| 6,403,580 B1 | 6/2002 | Himmelsbach et al. | |
| 6,617,329 B2 | 9/2003 | Himmelsbach et al. | |
| 6,627,634 B2 | 9/2003 | Himmelsbach et al. | |
| 6,653,305 B2 | 11/2003 | Himmelsbach et al. | |
| 6,656,946 B2 | 12/2003 | Himmelsbach et al. | |
| 6,673,803 B2 | 1/2004 | Thomas et al. | |
| 6,740,651 B2 | 5/2004 | Himmelsbach et al. | |
| 6,924,285 B2 | 8/2005 | Himmelsbach et al. | |
| 6,972,288 B1 | 12/2005 | Himmelsbach et al. | |
| 7,019,012 B2 | 3/2006 | Himmelsbach et al. | |
| 7,084,136 B2 | 8/2006 | Tanimoto et al. | |
| 7,119,084 B2 | 10/2006 | Himmelsbach et al. | |
| 7,160,889 B2 | 1/2007 | Hennequin et al. | |
| 7,196,091 B2 | 3/2007 | Himmelsbach et al. | |
| 7,220,750 B2 | 5/2007 | Himmelsbach et al. | |
| 7,223,749 B2 | 5/2007 | Himmelsbach et al. | |
| 7,456,189 B2 | 11/2008 | Himmelsbach et al. | |
| 7,846,936 B2 | 12/2010 | Hilberg et al. | |
| 7,960,546 B2 | 6/2011 | Schroeder et al. | |
| 8,067,593 B2 | 11/2011 | Schroeder et al. | |
| RE43,431 E | 5/2012 | Himmelsbach et al. | |
| 8,188,274 B2 | 5/2012 | Schroeder et al. | |
| 2001/0044435 A1 | 11/2001 | Himmelsbach et al. | |
| 2002/0077330 A1 | 6/2002 | Himmelsbach et al. | |
| 2002/0082270 A1 | 6/2002 | Himmelsbach et al. | |
| 2002/0169180 A1 | 11/2002 | Himmelsbach et al. | |
| 2002/0173509 A1 | 11/2002 | Himmelsbach et al. | |
| 2003/0225079 A1 | 12/2003 | Singer et al. | |
| 2005/0043233 A1 | 2/2005 | Stefanic et al. | |
| 2005/0085495 A1 | 4/2005 | Soyka et al. | |
| 2005/0159436 A1 | 7/2005 | Himmelsbach et al. | |
| 2005/0215574 A1 | 9/2005 | Bradbury et al. | |
| 2006/0058311 A1 | 3/2006 | Munzert et al. | |
| 2006/0100223 A1 | 5/2006 | Himmelsbach et al. | |
| 2006/0270672 A1 | 11/2006 | Himmelsbach et al. | |
| 2007/0027170 A1 | 2/2007 | Soyka et al. | |
| 2007/0078091 A1 | 4/2007 | Hubler et al. | |
| 2007/0099918 A1 | 5/2007 | Singer et al. | |
| 2007/0185091 A1 | 8/2007 | Himmelsbach et al. | |
| 2008/0103161 A1 | 5/2008 | Himmelsbach et al. | |
| 2008/0254040 A1 | 10/2008 | Stefanic et al. | |
| 2008/0269487 A1 | 10/2008 | Bradbury et al. | |
| 2009/0036676 A1 | 2/2009 | Himmelsbach et al. | |
| 2009/0203683 A1 | 8/2009 | Himmelsbach et al. | |
| 2009/0238828 A1 | 9/2009 | Munzert et al. | |
| 2009/0306044 A1 | 12/2009 | Solca et al. | |
| 2009/0306101 A1 | 12/2009 | Solca et al. | |
| 2009/0306378 A1 | 12/2009 | Schroeder et al. | |

(Continued)

FOREIGN PATENT DOCUMENTS

DE 19825591 A 12/1999
DE 19911366 A1 9/2000

(Continued)

OTHER PUBLICATIONS

Bell, D.W. et al., "Inherited susceptibility to lung cancer may be associated with the T790M drug resistance mutation in EGFR". Nature Genetics, Dec. 2005, vol. 37, No. 12, p. 1315-1316. Published online Oct. 30, 2005.

(Continued)

*Primary Examiner* — Paul Zarek
(74) *Attorney, Agent, or Firm* — Michael P. Morris; Anthony P. Bottino

(57) ABSTRACT

The present invention relates to the use of specific EGF-receptor antagonists for preparing a pharmaceutical composition for the prevention and/or treatment of benign prostatic hyperplasia and/or prostatic hypertrophy, a method for the treatment or prevention of benign prostatic hyperplasia/prostatic hypertrophy comprising administering an EGF-receptor antagonist of groups (A), (B) or (C), described herein optionally in combination with known compounds for the treatment of benign prostatic hyperplasia/prostatic hypertrophy, as well as associated pharmaceutical compositions.

1 Claim, No Drawings

U.S. PATENT DOCUMENTS

| | | | |
|---|---|---|---|
| 2009/0318480 A1 | 12/2009 | Solca |
| 2010/0010023 A1 | 1/2010 | Himmelsbach et al. |
| 2010/0069414 A1 | 3/2010 | Himmelsbach et al. |
| 2011/0039863 A1 | 2/2011 | Hilberg et al. |
| 2011/0046168 A1 | 2/2011 | Himmelsbach et al. |
| 2011/0142929 A1 | 6/2011 | Messerschmid et al. |
| 2011/0171289 A1 | 7/2011 | Stefanic et al. |
| 2011/0207929 A1 | 8/2011 | Schroeder et al. |
| 2011/0207932 A1 | 8/2011 | Schroeder et al. |
| 2012/0107399 A1 | 5/2012 | Barta |
| 2012/0157472 A1 | 6/2012 | Larsen et al. |
| 2012/0329778 A1 | 12/2012 | Himmelsbach et al. |
| 2013/0012465 A1 | 1/2013 | Haslinger et al. |

FOREIGN PATENT DOCUMENTS

| | | | |
|---|---|---|---|
| DE | 10017539 A1 | 10/2001 |
| DE | 10042060 A1 | 3/2002 |
| DE | 10042064 | 3/2002 |
| EP | 0566226 A1 | 10/1993 |
| EP | 0799619 A2 | 10/1997 |
| EP | 1123705 A1 | 8/2001 |
| WO | 9630347 | 10/1996 |
| WO | 9633980 | 10/1996 |
| WO | 9702266 | 1/1997 |
| WO | 9738983 A1 | 10/1997 |
| WO | 9843960 A1 | 10/1998 |
| WO | 9909016 | 2/1999 |
| WO | 9933980 | 7/1999 |
| WO | 9935146 | 7/1999 |
| WO | 9965228 | 12/1999 |
| WO | 0031048 | 6/2000 |
| WO | 0078735 | 12/2000 |
| WO | 0134574 | 5/2001 |
| WO | 0168186 | 9/2001 |
| WO | 0241882 A2 | 5/2002 |
| WO | 0250043 A1 | 6/2002 |
| WO | 03094921 A1 | 11/2003 |
| WO | 2004096224 A2 | 11/2004 |
| WO | 2005037824 A2 | 4/2005 |
| WO | 2006018182 A1 | 2/2006 |
| WO | 2007054550 A1 | 5/2007 |
| WO | 2007054551 A1 | 5/2007 |
| WO | 2007085638 A1 | 8/2007 |
| WO | 2008034776 A1 | 3/2008 |
| WO | 2009147238 A1 | 12/2009 |
| WO | 2010081817 A1 | 7/2010 |
| WO | 2011003853 A2 | 1/2011 |
| WO | 2011069962 A1 | 6/2011 |

OTHER PUBLICATIONS

Cancer Genome and Collaborative Group. Nature, Brief Communications, Sep. 2004, vol. 431, p. 525-526.

Harari, P.M. "Epidermal growth factor receptor inhibition strategies in oncology". Endocrine-Related Cancer, 2004, vol. 11. p. 689-708.

Krozely, P. Abstract—Clinical Journal of Oncology Nursing, 2004, vol. 8, No. 2, p. 1092-1095.

Paez, J. G. "EGFR Mutations in Lung Cancer: Correlation with Clinical Response to Gefitinib Therapy". Science, vol. 304, 2004, p. 1497-1500.

Yanase, K. et al., "Gefitinib reverses breast cancer resistance protein-medicated drug resistance". Molecular Cancer Therapeutics, 2004, Vo. 9, No. 9, p. 119-1125.

Abstract in English (2000) for DE19911366.

Barton, J. et al., "Growth Factors and their Receptors: new Targets for Prostate Cancern Therapy". Urology 58 (Supplement 2A), Aug. 2001, p. 114-122.

Duque, J.L. et al., "Heparin-Binding Epidermal Growth Factor-Like Growth Factor is an Autocrine Mediator of Human Prostate Stromal Cell Growth in Vitro". The Journal of Urology, vol. 165, Jan. 2001, p. 284-288.

Herbst, R.S. et al., "Monoclonal Antibodies to Target Epidermal Growth Factor Receptor-Positive Tumors". Cancer, Mar. 1, 2002, vol. 94, No. 5, p. 1593-1611.

International Search Report for PCT/EP2003/04606 mailed Dec. 1, 2003.

Tsou, Hwei-Ru, "6-Substituted-4-(3-bromophenylamino)quinazolines as Putative Irreversible Inhibitors of the Epidermal Growth Factor Receptor (EGFR) and Human Epidermal Growth Facotr Receptor (HER-2) Tyrosine Kinases with Enhanced Antitumore Activity", J. Med. Chem 2001, 2719-2734, vol. 44.

U.S. Appl. No. 12/914,003, filed Oct. 28, 2010, Inventor: Frank Himmelsbach.

Lee, Mary, "Tamsulosin for the Treatment of Benign Prostatic Hypertrophy," The Annals of Pharmacotherapy, Feb. 2000,vol. 34, pp. 188-199.

Alan, Rick, "Benign Prostatic Hyperplasia (BPH)", available at http://healthlibrary.epnet.com/GetContent. aspx?token-1baaea3c-d4f5-4e14-8429-e3b3e1add7a7^chunkiid-12003, 2006.

Maria P. De Miguel et al., Immunohistochemical Comparative Analysis of Transforming Growth Factor alpha, Epidermall Growth Factor, and Epidermal LGrowth Factor Receptor in normal, hyperplastic and neoplastic human prostates, Cytokine Septemer 1999, vol. 11, No. 9, pp. 722-727.

Gonzalez-Barcena et al.; Responses to the antagonistic analog of LH-RH (SB-75, Cetrorelix) in patients with benign prostatic hyperplasia and prostatic cancer; The Prostate; 1994; 24(2); 84-92; only abstract provided.

Hoffman; Chapter 10 Catecholamines, Sympathomimetic Drugs, and Adrenergic Receptor Antagonists; Goodman & Gilman's The Pharmacological Basis of Therapeutics, 10th ed.; Hardman JG; Limbird LD; and Gilman AG; Eds., McGraw-Hill; 2001; 215-268 (pp. 215, 247 and 248 provided).

Rayford et al.; Muscarinic cholinergic receptors promote growth of human prostate cancer cells; The Prostate; Feb. 1997; 30(3); 160-166.

USE OF INHIBITORS OF THE EGFR-MEDIATED SIGNAL TRANSDUCTION FOR THE TREATMENT OF BENIGN PROSTATIC HYPERPLASIA (BPH)/PROSTATIC HYPERTROPHY

RELATED APPLICATIONS

This application is a continuation of U.S. application Ser. No. 11/609,407, filed Dec. 12, 2006, which claims benefit to U.S. Application Ser. No. 60/389,815 filed Jun. 18, 2003 and DE10221018, filed May 11, 2002.

The present invention relates to the use of EGF-receptor antagonists which are selected from the group (A) consisting of the compounds of general formula

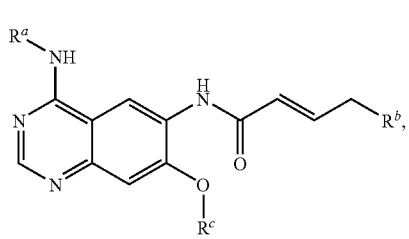

(I)

wherein $R^a$, $R^b$ and $R^c$ are defined as in claim 1,
the group (B) consisting of the compounds
(1) 4-[(3-chloro-4-fluorophenyl)amino]-6-[3-(morpholin-4-yl)-propyloxy]-7-methoxy-quinazoline,
(2) 4-[(3-ethynylphenyl)amino]-6,7-bis-(2-methoxyethoxy)-quinazoline,
(3) 4-[(3-chloro-4-fluorophenyl)amino]-7-[3-(morpholin-4-yl)-propyloxy]-6-[(vinyl-carbonyl)amino]-quinazoline,
(4) 4-[(R)-(1-phenyl-ethyl)amino]-6-(4-hydroxy-phenyl) 7H-pyrrolo[2,3-d]pyrimidine,
(5) 3-cyano-4-[(3-chloro-4-fluorophenyl)amino]-6-{[4-(N, N-dimethylamino)-1-oxo-2-buten-1-yl]amino}-7-ethoxy-quinoline or
(6) 4-{[3-chloro-4-(3-fluorobenzyloxy)-phenyl]amino}-6-(5-{[(2-methanesulphonyl-ethyl)amino]methyl}-furan-2-yl)-quinazoline and
the group (C) consisting of the antibodies Cetuximab, Trastuzumab, ABX-EGF and Mab ICR-62,
and, in the case of the compounds of groups (A) and (B), optionally the tautomers, the stereoisomers or the salts thereof, particularly the physiologically acceptable salts thereof with inorganic or organic acids or bases, for preparing a pharmaceutical composition for the prevention and/or treatment of benign prostatic hyperplasia (BPH) and/or prostatic hypertrophy, a method for the treatment or prevention of benign prostatic hyperplasia/prostatic hypertrophy comprising administering an EGF-receptor antagonist of groups (A), (B) or (C), optionally in combination with known compounds for the treatment of benign prostatic hyperplasia/prostatic hypertrophy, as well as pharmaceutical compositions comprising an EGF-receptor antagonist of groups (A), (B) or (C) and a known compound for the treatment of benign prostatic hyperplasia/prostatic hypertrophy, selected from the group (D) consisting of osaterone, α1-adrenoreceptor-antagonists, non-selective and selective muscarine antagonists, LHRH-/GnRH-antagonists or testosterone-5α-reductase inhibitors.

The α1-adrenoreceptor-antagonists used in the combination of active substances according to the invention are preferably the active substances KMD-3231 (silodosin), A10-8507L, UK-338003, RBX-2258 (parvosin), SNAP-6383 (L 771688), GYKI-16084, UK-294315, (S)-doxazosin, tamsulosin, prazosin, naftopidil, terazosin, alfuzosin or indoramin.

Examples of non-selective and selective muscarine antagonists which may be used in the combination of active substances according to the invention are preferably the active substances darifenacin or tolterodine.

Examples of LHRH-/GnRH-antagonists which may be used in the combination of active substances according to the invention are preferably the active substances goserelin, desorelin, cetrorelix or gonadorelin.

Examples of testosterone-5α-reductase inhibitors which may be used in the combination of active substances according to the invention are preferably the active substances GI-198745 (dutasteride), LY-320236 (izonsteride), TF 505, AS-601811, finasteride, FK-687 or CS-891.

BACKGROUND TO THE INVENTION

Benign prostatic hyperplasia (BPH)/prostatic hypertrophy, a benign enlargement of the prostate, is a well-known complaint in men, which generally comes to medical attention from the age of 50 onwards. About 50% of all men aged over 50 and 95% of all men aged over 70 are affected by it. Benign prostatic hyperplasia/prostatic hypertrophy is a generally progressive condition which in serious cases may endanger kidney function and require surgical intervention. The number of untreated patients runs at over 37 million worldwide. The growth of the prostate compresses or lengthens the urethra, causing the symptoms of ureteral blockage and possibly leading to urinary retention.

The prostate consists of epithelial glandular tubes embedded in fibromuscular stroma. The hyperplastic growth of the prostate begins at about the age of 30 in the periurethrally located parts of the gland, the so-called transition zone. Apart from the effects of ageing, androgenic hormones constitute a crucial stimulus to growth in the post-pubertal regulation of the volume of the gland. In the normal prostate, the enzyme 5α-reductase in the epithelial cells converts the androgenic hormone testosterone (T) into dihydrotestosterone (DHT). DHT, an active androgenic prostate metabolite, binds to cytoplasmic receptors and is transported into the cell nucleus where it initiates RNA and protein synthesis and cell replication. It is assumed that BPH occurs in response to the effects of DHT on the ageing prostate and to changes in the stroma and epithelial cells (Steers, Zorn, *Dis. Mon.*, 41(7):437-497 (1995)).

Age-dependent changes in the serum concentrations of the hormonal regulatory circuit as a whole (LH, FSH, SHGB, T and DHT), and of other hormones which may affect this regulatory circuit (oestrogens, prolactin, testosterone derivatives), have been investigated as possible causes. However, there is no correlation between age-dependent hormonal changes in the serum and the intraprostatic hormone concentrations. Thus, it is clear that the prostate itself is responsible for regulating the hormonal milieu.

Possible points of attack for controlling the intraprostatic hormonal milieu are the 5α-reductase (i.e. the androgen metabolism), hormone receptor expression in the epithelium and stroma, oestrogens and other hormones. In addition, numerous peptidal growth factors have a paracrine or autocrine effect on the local metabolism in the various compartments of the gland, by means of which the equilibrium of the cell kinetics can be shifted between proliferation and programmed cell death.

The clinical symptoms of BPH comprise both blocking symptoms (e.g. stoppage of the stream of urine, a weak or interrupted stream, urinary retention) which result directly from the constriction of the neck of the bladder and the prostatic urethra by the hyperplastic prostate, and also symptoms of an irritated lower urinary tract (e.g. urinary frequency, nycturia, dysuria, uresiesthesis, urinary incontinence). Untreated, BPH may lead to serious complications of the urinary tract and kidneys such as e.g. acute urinary retention and hydronephrosis (uronephrosis).

DESCRIPTION OF THE INVENTION

An object of the present invention is to find new active substances for the prevention and/or treatment of benign prostatic hyperplasia/prostatic hypertrophy.

Surprisingly it has been found that the EGF-receptor antagonists of the abovementioned groups (A) to (C) are particularly suitable for the prevention and/or treatment of benign prostatic hyperplasia/prostatic hypertrophy.

In general formula (I)

$R^a$ denotes a phenyl, benzyl or 1-phenylethyl group, wherein the phenyl nucleus is substituted in each case by the groups $R^1$ and $R^2$, where
  $R^1$ and $R^2$, which may be identical or different, in each case denote a hydrogen, fluorine, chlorine or bromine atom, a methyl, trifluoromethyl, ethynyl or methoxy group,
$R^b$ denotes a di-($C_{1-4}$-alkyl)-amino group wherein the alkyl moieties may be identical or different,
  an N—($C_{1-4}$-alkyl)-N—($C_{2-4}$-alkyl)amino group wherein the $C_{2-4}$-alkyl moiety in the position β, γ or δ to the nitrogen atom of the amino group is substituted by the group $R^4$, where
    $R^4$ denotes a $C_{1-3}$-alkoxy or di-($C_{1-3}$-alkyl)-amino group, a pyrrolidino, piperidino or morpholino group,
  a di-($C_{2-4}$-alkyl)-amino group wherein the two $C_{2-4}$-alkyl moieties in the position β, γ or δ to the nitrogen atom of the amino group are each substituted by the group $R^4$, while the substituents may be identical or different and $R^4$ is as hereinbefore defined,
  a $C_{1-4}$-alkylamino group wherein the nitrogen atom is substituted by a tetrahydrofuran-3-yl, tetrahydropyran-3-yl, tetrahydropyran-4-yl, tetrahydrofuranylmethyl, 1-($C_{1-2}$-alkyl)pyrrolidin-3-yl, 1-($C_{1-2}$-alkyl)piperidin-3-yl or 1-($C_{1-2}$-alkyl)piperidin-4-yl group,
  a $C_{3-5}$-cycloalkylamino or $C_{3-5}$-cycloalkyl-$C_{1-3}$-alkylamino group, wherein in each case the nitrogen atom is substituted by a $C_{1-3}$-alkyl group,
  a 5- to 7-membered alkyleneimino group optionally substituted by 1 or 2 methyl groups which may be substituted by the group $R^4$ either at a cyclic carbon atom or at one of the methyl groups, where $R^4$ is as hereinbefore defined,
  a piperidino group optionally substituted by 1 or 2 methyl groups wherein the methylene group in the 4 position is replaced by an oxygen or sulphur atom, by a sulphinyl or sulphonyl group or by an imino group substituted by the group $R^5$, where $R^5$ denotes a $C_{1-3}$-alkyl, 2-methoxyethyl, 3-methoxypropyl, $C_{3-6}$-cycloalkyl, $C_{3-6}$-cycloalkyl-$C_{1-3}$-alkyl, $C_{1-3}$-alkylcarbonyl, $C_{1-3}$-alkylsulphonyl, aminocarbonyl, $C_{1-3}$-alkylaminocarbonyl or di-($C_{1-3}$-alkyl)-aminocarbonyl group, and
$R^c$ denotes a $C_{4-7}$-cycloalkoxy or $C_{3-7}$-cycloalkyl-$C_{1-4}$-alkoxy group, wherein the cycloalkyl moiety may be substituted in each case by a $C_{1-3}$-alkyl or $C_{1-3}$-alkoxy group, or
a tetrahydrofuran-3-yloxy, tetrahydropyran-3-yloxy, tetrahydropyran-4-yloxy or tetrahydrofuranylmethoxy group.

Within the scope of the objects according to the invention, preferred EGF-receptor antagonists are those which are selected from the group (A') consisting of compounds of general formula (I) wherein
$R^a$ denotes a phenyl group substituted by the groups $R^1$ and $R^2$, where
  $R_1$ denotes a fluorine, chlorine or bromine atom and
  $R_2$ denotes a hydrogen or a fluorine atom,
$R^b$ denotes a di-($C_{1-4}$-alkyl)-amino group wherein the alkyl moieties may be identical or different,
  a methylamino or ethylamino group, wherein in each case the nitrogen atom is substituted by a 2-methoxy-ethyl, 1-methoxy-2-propyl, 2-methoxy-propyl, 3-methoxy-propyl, tetrahydrofuran-3-yl, tetrahydropyran-4-yl, tetrahydrofuran-2-ylmethyl, 1-methyl-piperidin-4-yl, 1-ethyl-piperidin-4-yl, 1-(tetrahydrofuran-3-yl)-piperidin-4-yl, cyclopropyl or cyclopropylmethyl group,
  a bis-(2-methoxyethyl)-amino group,
  a pyrrolidino, piperidino or morpholino group optionally substituted by one or two methyl groups,
  a piperazino group which is substituted in the 4 position by a methyl, ethyl, cyclopropyl, cyclopropylmethyl, 2-methoxy-ethyl, tetrahydrofuran-3-yl, tetrahydropyran-4-yl or tetrahydrofuran-2-ylmethyl group,
  a 2-(methoxymethyl)-pyrrolidino, 2-(ethoxymethyl)-pyrrolidino, 4-hydroxy-piperidino, 4-methoxy-piperidino, 4-ethoxy-piperidino, 4-(tetrahydrofuran-3-yl)-piperidino or 4-morpholino-piperidino group and
$R^c$ denotes a cyclopropylmethoxy, cyclobutylmethoxy, cyclopentylmethoxy or cyclohexylmethoxy group,
a cyclobutyloxy, cyclopentyloxy or cyclohexyloxy group,
a tetrahydrofuran-3-yloxy, tetrahydropyran-4-yloxy or tetrahydrofuran-2-ylmethoxy group
or are selected from the active substances of the abovementioned groups (B) and (C),
and, in the case of the compounds of groups A' and B, optionally the tautomers, the stereoisomers or the salts thereof.

Within the scope of the objects according to the invention, particularly preferred EGF-receptor antagonists are those which are selected from the group (A'') consisting of the compounds of general formula (I) wherein
$R^a$ denotes a 3-chloro-4-fluorophenyl group,
$R^b$ denotes a dimethylamino, diethylamino, bis-(2-methoxyethyl)-amino, N-methyl-N-(2-methoxy-ethyl)-amino, N-ethyl-N-(2-methoxy-ethyl)-amino, N-methyl-N-cyclopropyl-amino, N-methyl-N-cyclopropylmethyl-amino, N-methyl-N-(1-methoxy-2-propyl)-amino, N-methyl-N-(2-methoxy-propyl)-amino, N-methyl-N-(3-methoxy-propyl)-amino, N-methyl-N-(tetrahydrofuran-3-yl)-amino, N-methyl-N-(tetrahydropyran-4-yl)-amino, N-methyl-N-(tetrahydrofuran-2-ylmethyl)-amino or N-methyl-N-(1-methyl-piperidin-4-yl)-amino group
a pyrrolidino, piperidino or morpholino group optionally substituted by one or two methyl groups, a piperazino group which is substituted in the 4 position by a methyl, ethyl, cyclopropylmethyl or 2-methoxy-ethyl group, and $R^c$ denotes a cyclopropylmethoxy, cyclobutyloxy or cyclopentyloxy group, a tetrahydrofuran-3-yloxy or tetrahydrofuran-2-ylmethoxy group or are selected from the active substances of the abovementioned groups (B) and (C), and, in the case of the compounds of groups (A") and (B), optionally the tautomers, the stereoisomers or the salts thereof.

Within the scope of the objects according to the invention, the following compounds of the abovementioned groups (A), (B) and (C) may be used, for example:

(1) 4-[(3-chloro-4-fluorophenyl)amino]-6-{[4-(morpholin-4-yl)-1-oxo-2-buten-1-yl]amino}-7-cyclopropylmethoxy-quinazoline, (2) 4-[(3-chloro-4-fluorophenyl)amino]-6-{[4-(N,N-diethylamino)-1-oxo-2-buten-1-yl]amino}-7-cyclopropyl-methoxy-quinazoline, (3) 4-[(3-chloro-4-fluorophenyl)amino]-6-{[4-(dimethylamino)-1-oxo-2-buten-1-yl]amino}-7-cyclopropyl-methoxy-quinazoline, (4) 4-[(3-chloro-4-fluorophenyl)amino]-6-({4-[bis-(2-methoxyethyl)-amino]-1-oxo-2-buten-1-yl}amino)-7-cyclopropylmethoxy-quinazoline, (5) 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, (6) 4-[(3-chloro-4-fluorophenyl)amino]-6-{[4-(N,N-dimethylamino)-1-oxo-2-buten-1-yl]amino}-7-cyclopentyloxy-quinazoline, (7) 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, (8) 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, (9) 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline,

(10) 4-[(3-chloro-4-fluorophenyl)amino]-6-{[4-(N-cyclopropyl-N-methyl-amino)-1-oxo-2-buten-1-yl]amino}-7-cyclopentyloxy-quinazoline,

(11) 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline,

(12) 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline,

(13) 4-[(3-chloro-4-fluorophenyl)amino]-6-[3-(morpholin-4-yl)-propyloxy]-7-methoxy-quinazoline,

(14) 4-[(3-ethynylphenyl)amino]-6,7-bis-(2-methoxy-ethoxy)-quinazoline,

(15) 4-[(3-chloro-4-fluorophenyl)amino]-7-[3-(morpholin-4-yl)-propyloxy]-6-[(vinylcarbonyl)amino]-quinazoline,

(16) 4-[(R)-(1-phenyl-ethyl)amino]-6-(4-hydroxy-phenyl)-7H-pyrrolo[2,3-d]-pyrimidine,

(17) 3-cyano-4-[(3-chloro-4-fluorophenyl)amino]-6-{[4-(N,N-dimethylamino)-1-oxo-2-buten-1-yl]amino}-7-ethoxy-quinoline,

(18) 4-{[3-chloro-4-(3-fluorobenzyloxy)-phenyl]amino}-6-(5-{[(2-methanesulphonyl-ethyl)amino]methyl}-furan-2-yl)quinazoline, the tautomers, the stereoisomers or the salts thereof, the antibodies Cetuximab, Trastuzumab, ABX-EGF or Mab ICR-62, while according to the invention most particular importance is attached to the compounds:

(1) 4-[(3-chloro-4-fluorophenyl)amino]-6-{[4-(morpholin-4-yl)-1-oxo-2-buten-1-yl]amino}-7-cyclopropylmethoxy-quinazoline, (2) 4-[(3-chloro-4-fluorophenyl)amino]-6-{[4-(N,N-diethylamino)-1-oxo-2-buten-1-yl]amino}-7-cyclopropyl-methoxy-quinazoline, (3) 4-[(3-chloro-4-fluorophenyl)amino]-6-{[4-(dimethylamino)-1-oxo-2-buten-1-yl]amino}-7-cyclopropyl-methoxy-quinazoline, (4) 4-[(3-chloro-4-fluorophenyl)amino]-6-{[4-(N,N-dimethylamino)-1-oxo-2-buten-1-yl]amino}-7-cyclopentyloxy-quinazoline, (5) 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, (6) 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, (7) 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, (8) 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, (9) 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline or

(10) 4-[(3-chloro-4-fluorophenyl)amino]-6-[3-(morpholin-4-yl)-propyloxy]-7-methoxy-quinazoline,

(11) 4-[(3-ethynylphenyl)amino]-6,7-bis-(2-methoxy-ethoxy)-quinazoline,

(12) 4-[(3-chloro-4-fluorophenyl)amino]-7-[3-(morpholin-4-yl)-propyloxy]-6-[(vinylcarbonyl)amino]-quinazoline,

(13) 3-cyano-4-[(3-chloro-4-fluorophenyl)amino]-6-{[4-(N,N-dimethylamino)-1-oxo-2-buten-1-yl]amino}-7-ethoxy-quinoline,

(14) 4-{[3-chloro-4-(3-fluorobenzyloxy)-phenyl]amino}-6-(5-{[(2-methanesulphonyl-ethyl)amino]methyl}-furan-2-yl)quinazoline, the tautomers, the stereoisomers or the salts thereof, but especially to the compounds:

(1) 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, (2) 4-[(3-chloro-4-fluorophenyl)amino]-6-{[4-(N-cyclopropyl-N-methyl-amino)-1-oxo-2-buten-1-yl]amino}-7-cyclopentyloxy-quinazoline or (3) 4-[(3-chloro-4-fluorophenyl)amino]-6-{[4(N,N-dimethylamino)-1-oxo-2-buten-1-yl]amino}-7-[(S)-(tetrahydrofuran-2-yl)methoxy]-quinazoline, the tautomers, the stereoisomers or the salts thereof.

In addition, combinations of the abovementioned active substances with other substances already on the market for the treatment of benign prostatic hyperplasia/prostatic hypertrophy may also be used according to the invention.

The invention thus also relates to a method for the treatment or prevention of benign prostatic hyperplasia/prostatic hypertrophy by simultaneous or sequential administration of a therapeutically effective amount of an active substance of the abovementioned group (A), (B) or (C) in combination with a therapeutically effective amount of another medicament active against benign prostatic hyperplasia/prostatic hypertrophy (D) to a person in need of such a treatment.

The medicament (D) may be selected from the group consisting of osaterone, an α1-adrenoreceptor antagonist, non-selective and selective muscarine antagonists, LHRH/GnRH antagonists and a testosterone-5α-reductase inhibitor.

The α1-adrenoreceptor antagonist may be selected from the group consisting of the active substances KMD-3231 (selodosin), A10-8507L, UK-338003, RBX-2258 (parvosin), SNAP-6383 (L 771688), GYKI-16084, UK-294315, (S)-doxazosin, tamsulosin, prazosin, naftopidil, terazosin, alfuzosin and indoramin.

The non-selective or selective muscarine antagonist may be selected from the group consisting of the active substances darifenacin and tolterodine.

The LHRH/GnRH antagonist may be selected from the group consisting of the active substances goserelin, desorelin, cetrorelix and gonadorelin.

The testosterone-5α-reductase inhibitor may be selected from the group consisting of the active substances GI-198745 (dutasteride), LY-320236 (izonsteride), TF 505, AS-601811, finasteride, FK-687 and CS-891.

In a preferred embodiment of the process according to the invention the medicament (D) is selected from the group consisting of tamsulosin, UK-338003, terazosin, indoramin, tolterodine, dutasteride and finasteride.

In a particularly preferred embodiment of the process according to the invention tamsulosin is used.

The dosage of components (A), (B) and (C) is 0.01 mg to 500 mg administered up to 5 times a day, preferably 0.01 mg to 300 mg up to 3 times a day.

The dosage of component (D) for the combination of pharmaceutical compositions is roughly from 1/10 of the lowest normally recommended dose to 1/1 of the normally recommended dose.

An EGF receptor antagonist of group (A), (B) or (C) as mentioned above may for example be administered in combination with
tamsulosin, which may be administered orally in a dosage of 0.2 to 0.8 mg once a day, or in combination with
naftopidil, which may be administered orally in a dosage of 25 to 100 mg per day, or in combination with
terazosin, which may be administered orally in a dosage of 1 to 20 mg per day, or in combination with
alfuzosin, which may be administered orally in a dosage of 2.5 mg three times a day to 10 mg once a day, or in combination with
indoramin, which may be administered orally in a dosage of 50 to 200 mg per day, or in combination with
doxazosin, which may be administered orally in a dosage of 1 to 16 mg per day, or in combination with
dutasteride, which may be administered orally in a dosage of 0.5 mg per day, or in combination with
finasteride, which may be administered orally in a dosage of 1 to 5 mg per day, or in combination with
tolterodine, which may be administered orally in a dosage of 2 to 4 mg per day, for the treatment of benign prostatic hyperplasia/prostatic hypertrophy.

In addition a pharmaceutical composition according to the invention may be a kit of parts for the treatment and/or prevention of benign prostatic hyperplasia/prostatic hypertrophy, this kit comprising:
(a) a first container containing a pharmaceutical composition comprising a therapeutically effect amount of an active substance selected from groups (A), (B) or (C) and one or more pharmaceutically acceptable diluents and/or carriers; and
(b) a second container containing a pharmaceutical composition comprising one of the medicaments (D) and one or more pharmaceutically acceptable diluents and/or carriers.

A preferred kit comprises tamsulosin in the second container.

In another aspect the present invention relates to the use of an active substance selected from groups (A), (B) or (C) in combination with another medicament (D) for the preparation of a pharmaceutical composition for the treatment and/or prevention of benign prostatic hyperplasia/prostatic hypertrophy.

The active substances of groups (A) to (D) which may be used for this purpose according to the invention as well as preferred embodiments can be found in the comments relating to the objects of the invention mentioned above.

The active substances may be administered orally, parenterally, by spray inhalation or rectally. Parenteral administration may consist of subcutaneous, intravenous and intramuscular injections.

For this purpose, conventional formulations may be used. For example, the active substances, optionally combined with other active substances, may be formulated with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The active substances may be administered orally in a wide variety of different dosage forms, for example they may be formulated together with different pharmaceutically acceptable inert carriers in the form of tablets, capsules, pastilles, lozenges, hard sweets, powders, atomisers, aqueous suspensions, elixirs, syrups and the like. Such carriers include for example solid diluents or fillers, sterile aqueous media and various non-toxic organic solvents. In addition, oral formulations of this kind may be suitably sweetened and/or flavoured with various agents conventionally used for this purpose. In general, the active substances are present in oral formulations of this kind at concentration levels ranging from about 0.5 wt. % to about 90 wt. %, based on the total composition, in amounts sufficient to produce the desired dosage units. Other suitable dosage forms for the active substances comprise formulations for controlled release and devices which are well known to specialists in the field.

For the purposes of parenteral administration, solutions of the active substances in sesame or groundnut oil or in aqueous propylene glycol may be used, as well as sterile aqueous solutions of the corresponding pharmaceutically acceptable salts. Such aqueous solutions should if necessary be suitably buffered and the liquid diluent made isotonic with sufficient salt or glucose. These specific aqueous solutions are particularly suitable for intravenous, intramuscular and subcutaneous injections. In connection with this, the sterile aqueous media used may easily be obtained using common methods well known in the art. For example, distilled water is normally used as the liquid diluent, and the final preparation is passed through a suitable bacterial filter such as a filter made of sintered glass or kieselguhr or unglazed porcelain. Preferred filters of this kind include the Berkefeld, Chamberland and asbestos disc metal Seitz filter, in which the fluid is sucked into a sterile container by means of a suction pump. During the preparation of these injectable solutions the necessary process steps should be taken at all times to ensure that the end products are obtained in a sterile condition. For the purposes of transdermal administration, the dosage form of the particular compound or compounds may comprise, for example, solutions, lotions, ointments, creams, gels, suppositories, formulations for sustained rate-limited release and equipment for this purpose. Such dosage forms comprise the particular compound or compounds and may contain ethanol, water, penetration promoters and inert carriers such as gel producers, mineral oil, emulsifiers, benzyl alcohol and the like.

The compounds are administered by inhalation in the form of powdered preparations with lactose and other excipients or in the form of aqueous solutions as aerosols.

The inhalable powders which may be used within the scope of the use according to the invention may contain the active substance or combination of active substances either on their own or in admixture with suitable physiologically acceptable excipients. If the active substance or combination of active substances is present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred. Lactose is particularly preferred, while lactose monohydrate is most preferred, as the excipient according to the invention.

The propellant-containing aerosols for inhalation which may be used within the scope of the use according to the invention may contain the active substance or combination of active substances dissolved in the propellant gas or in dispersed form. The propellant gases which may be used to prepare the aerosols for inhalation are known from the prior art. Suitable propellant gases are selected from among the hydrocarbons such as n-propane, n-butane or isobutane and halohydrocarbons such as preferably fluorinated derivatives of methane, ethane, propane, butane, cyclopropane or cyclobutane. The abovementioned propellant gases may be used on their own or mixed together. Particularly preferred propellant gases are fluorinated alkane derivatives selected from HFC134a (1,1,1,2-tetrafluoroethane), HFC227 (1,1,1,2,3,3,3-heptafluoropropane) and mixtures thereof.

The propellant-containing aerosols for inhalation which may be used within the scope of the use according to the invention may further contain additional ingredients such as cosolvents, stabilisers, surfactants, antioxidants, lubricants and pH adjusters. All these ingredients are known in the art.

If the active substance or combination of active substances according to the invention is administered by inhalation in the form of propellant-free solutions or suspensions, aqueous or alcoholic, preferably ethanolic solutions may be used as solvent. The solvent may be exclusively water or it may be a mixture of water and ethanol. The relative proportion of ethanol to water is not restricted, but the maximum limit is preferably up to 70 percent by volume, particularly up to 60 percent by volume and most preferably up to 30 percent by volume. Solutions or suspensions containing the active substance or combination of active substances are optionally adjusted with suitable acids to a pH of 2 to 7, preferably 2 to 5. This pH may be adjusted using acids selected from inorganic or organic acids. Examples of particularly suitable inorganic acids are hydrochloric acid, hydrobromic acid, nitric acid, sulphuric acid and/or phosphoric acid. Examples of particularly suitable organic acids are: ascorbic acid, citric acid, malic acid, tartaric acid, maleic acid, succinic acid, fumaric acid, acetic acid, formic acid and/or propionic acid and others. Preferred inorganic acids are hydrochloric acid and sulphuric acid. Of the organic acids, ascorbic acid, fumaric acid and citric acid are preferred. If desired, mixtures of the abovementioned acids may also be used, particularly in the case of acids which have other properties, in addition to their acidifying properties, e.g. as flavourings, antioxidants or complexing agents, such as for example citric acid or ascorbic acid. According to the invention, hydrochloric acid is most preferably used to adjust the pH.

The abovementioned compounds and their salts have valuable properties. They are particularly suitable for the prevention and/or treatment of benign prostatic hyperplasia/prostatic hypertrophy.

For example the following compounds compound a=4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, compound b=4-[(3-chloro-4-fluorophenyl)amino]-6-{[4-(N-cyclopropyl-N-methyl-amino)-1-oxo-2-buten-1-yl]amino}-7-cyclopentyloxy-quinazoline and compound c=4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline were tested for their prostate-reducing activity.

EXPERIMENTAL SECTION

1) Test Method:

Three groups of five male rats (about 7 weeks old and weighing about 185 g) are treated for 14-15 days with an EGF-R-TK inhibitor. The active substance is administered once a day as a suspension through an oesophageal tube. After the test period has ended the animals are killed, their prostates are removed and weighed.

The results of the series of tests are listed in the Tables that follow.

2) Test Results:

TABLE 1

Administration of compound a (length of treatment: 14 days)

| | Dosage group | | | |
| --- | --- | --- | --- | --- |
| | control | compound a | | |
| Dosage level | 0 mg/kg | 10 mg/kg | 30 mg/kg | 100 mg/kg |
| average absolute weight [g] | 0.4641 | 0.4100 | 0.3419* | 0.1099* |
| average relative weight [% of body weight] | 0.1913 | 0.1718 | 0.1473* | 0.0672* |
| average relative weight [% of the brain] | 23.64 | 20.62 | 17.07* | 5.55* |

*$p < 0.05$

TABLE 2

Administration of compound b (length of treatment: 14 days)

| | Dosage group | | | |
| --- | --- | --- | --- | --- |
| | control | compound b | | |
| Dosage level | 0 mg/kg | 10 mg/kg | 30 mg/kg | 100 mg/kg |
| average absolute weight [g] | 0.4641 | 0.3983* | 0.3989 | 0.1848* |
| average relative weight [% of body weight] | 0.1913 | 0.1622* | 0.1697 | 0.1191* |
| average relative weight [% of the brain] | 23.64 | 20.23* | 20.71* | 10.13* |

TABLE 2-continued

Administration of compound b (length of treatment: 14 days)

| | Dosage group | | |
|---|---|---|---|
| | control | compound b | |
| Dosage level | 0 mg/kg | 10 mg/kg | 30 mg/kg | 100 mg/kg |

*p < 0.05

TABLE 3

Administration of compound c (length of treatment: 15 days)

| | Dosage group | | |
|---|---|---|---|
| | control | compound c | |
| Dosage level | 0 mg/kg | 10 mg/kg | 30 mg/kg | 100 mg/kg |
| average absolute weight [g] | 0.4641 | 0.3854* | 0.2242* | 0.1463* |
| average relative weight [% of body weight] | 0.1913 | 0.1681 | 0.1117* | 0.0892* |
| average relative weight [% of the brain] | 23.64 | 19.67* | 11.50* | 7.63* |

*p < 0.05

The abovementioned compounds, the preparation of which has not already been described in the prior art, are obtained by the following method:

EXAMPLE 1

4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4.70 ml of oxalyl chloride are added dropwise to a solution of 4.50 g of bromocrotonic acid in 60 ml of methylene chloride. Then one drop of N,N-dimethylformamide is added. After about 30 minutes the development of gas has ceased and the reaction mixture is evaporated down in the rotary evaporator. The crude bromocrotonic acid chloride is taken up in 30 ml of methylene chloride and, while cooling with an ice bath, added dropwise to a solution of 7.00 g of 4-[(3-chloro-4-fluorophenyl)amino]-6-amino-7-cyclopropylmethoxy-quinazoline and 10.20 ml of Hünig base in 150 ml of tetrahydrofuran. The reaction mixture is stirred for about 1.5 hours while cooling with an ice bath and for a further two hours at ambient temperature. Then 5.20 g of N-(2-methoxy-ethyl)-N-methylamine are added and the reaction mixture is stirred overnight at ambient temperature. For working up it is diluted with methylene chloride and washed thoroughly with water. The organic phase is dried over magnesium sulphate and evaporated down. The crude product is purified by chromatography over a silica gel column with ethyl acetate followed by ethyl acetate/methanol (19:1) as eluant.

Yield: 5.07 g (51% of theory)

Mass spectrum (ESI$^-$): m/z=512, 514 [M-H]$^-$ $R_f$ value: 0.25 (silica gel, ethyl acetate/methanol=9:1)

The following compounds are obtained analogously to Example 1:

(1)  4-[(3-chloro-4-fluorophenyl)amino]-6-{[4-(N,N-dimethylamino)-1-oxo-2-buten-1-yl]amino}-7-cyclopentyloxy-quinazoline, (2)  4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, (3)  4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, (4)  4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, (5)  4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, (6)  4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, (7)  4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, (8)  4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, (9)  4-[(3-chloro-4-fluorophenyl)amino]-6-{[4-(N-cyclopropyl-N-methyl-amino)-1-oxo-2-buten-1-yl]amino}-7-cyclopentyloxy-quinazoline,

(10)  4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline,

(11)  4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline.

What is claimed is:

1. A method of treating benign prostatic hyperplasia and/or prostatic hypertrophy which comprises administering to a patient in need thereof a therapeutically effective amount of the compound 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline or a pharmaceutically acceptable salt thereof.

* * * * *